United States Patent [19]

Lipinski

[11] 4,080,454
[45] Mar. 21, 1978

[54] 5-M-TOLYLOXYURACIL, ANTI-ULCER AGENT

[75] Inventor: Christopher A. Lipinski, Waterford, Conn.

[73] Assignee: Pfizer Inc., New York, N.Y.

[21] Appl. No.: 706,123

[22] Filed: Jul. 16, 1976

[51] Int. Cl.$^2$ .......................................... A61K 31/505
[52] U.S. Cl. ................................... 424/251; 260/260
[58] Field of Search ........................................ 424/251

[56] References Cited

PUBLICATIONS

Chem. Abstr., vol. 60, 14504, (1964) + 7th Col. index, (1962–1966).

Primary Examiner—Frederick E. Waddell
Attorney, Agent, or Firm—Connolly and Hutz

[57] ABSTRACT 5-m-Tolyloxyuracil, in substantially pure form and also in unit dosage form in a pharmaceutically acceptable diluent. Its use in the treatment of peptic ulcer is claimed.

2 Claims, 1 Drawing Figure

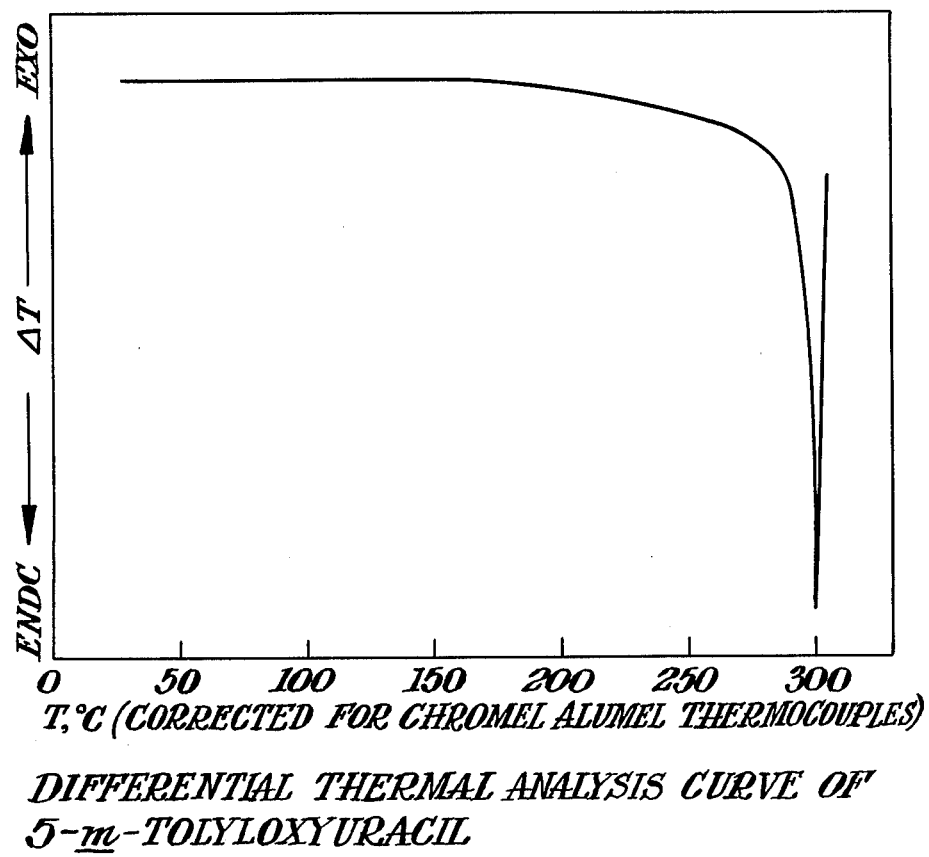
DIFFERENTIAL THERMAL ANALYSIS CURVE OF 5-m-TOLYLOXYURACIL

5-M-TOLYLOXYURACIL, ANTI-ULCER AGENT

BACKGROUND OF THE INVENTION

A number of 5-substituted phenoxyuracils are described in the chemistry literature. 5-Phenoxyuracil was first prepared by T. B. Johnson and H. H. Guest in Am. Chem. J., 42, 271 (1909). The same compound was prepared by B. R. Baker, J. L. Kelley in J. Med. Chem., 13, 461 (1970) and was tested as an inhibitor of FUDR phosphorylase and found to have poor activity. These same authors in a subsequent publication in J. Med. Chem., 14, 812 (1971) tested this same compound as an inhibitor of thymidine phosphorylase and found it to have poor activity.

A number of 5-substituted phenoxyuracils including unsubstituted phenoxy-, m-fluorophenoxy-, o-tolyloxy- and p-tolyloxyuracil were synthesized for cancer chemotherapeutic testing by Chun-Nien Chang, Shih-An Yang, Tien-Tu Wang and Yen Hu in Yao-Hsueh Pao 10, 600, 1963 (Acta Pharmaceutica Sinica 10, 600, and abstracted in CA 60: 14504b). In preliminary biological testing these authors found that m-fluorophenoxyuracil inhibited the growth of sarcoma 180 in mice.

A number of 5-substituted phenoxythiouracils are claimed in U.S. Pat. No. 2,697,708 and Brit. Pat. No. 706,253 as being active against Neurovaccinia infection. R. L. Thompson, M. Price, S. A. Minton, Jr., E. A. Falco and G. H. Hitchings in J. Immunol., 67, 483 (1951) describe the protection of mice against vaccinia virus by the administration of 5-substituted phenoxythiouracils. E. A. Falco, P. B. Russell and G. H. Hitchings in J. Am. Chem. Soc., 73, 4466 (1951) describe the preparation of some 5-substituted phenoxy 2-thiouracils including the preparation of 5-m-tolyloxy-2-thiouracil.

U.S. Pat. No. 3,154,551 describes the preparation of 2,4-dihydroxy-5-arylmercaptopyrimidines via the general method of condensing a thiophenol with 5-bromouracil. Brit. Pat. No. 951,431 describes similar compounds but neither of these patents discloses 5-(m-methylthiophenoxy)uracil or 5-(p-methylthiophenoxy)uracil. B. Roth and G. H. Hitchings in J. Org. Chem., 26, 2771 (1961) describe the inability of the authors to prepare 5-(p-methylphenoxy)uracil by reaction of 5-bromouracil with p-cresol.

Brit. Pat. No. 971,307 on the subject of 5-anilinopyrimidines describes the physical properties of 5-(m-methylanilino)uracil which was tested as an antibacterial and antimetabolic agent. Substantially the same subject matter is disclosed in U.S. Pat. No. 3,238,308. A subsequent publication by F. R. Geins, A. Perrotta and G. H. Hitchings in J. Med. Chem., 9, 108 (1966) discusses substantially similar subject matter.

M. R. Atkinson, G. Shaw and G. Sugowaz in J. Chem. Soc., 3207 (1957) describe the preparation of a number of 5-substituted phenylsulfonyl uracils as part of an antimetabolite study.

T. Zsolnai in Biochem. Pharmacol., 11, 995 (1962) describes the preparation of p-chloro- and p-methoxy-phenylhydrazinouracil for testing as fungistatic agents.

U.S. Pat. No. 3,922,345 on the subject matter of pyrimidinones having bronchodilator and antiulcer activities claims 5-(m-methylphenoxy)-2-(1H)pyrimidinone and the method of treating peptic ulcer which comprises administering to a subject afflicted therewith a daily dose of the above compound equivalent to about 0.60 to 21 mg. per kg. body weight. This patent also discloses the use of 4-hydroxy-5-(m-methylphenoxy)-pyrimidine as a bronchodilator.

We have discovered that in rats, monkeys and human subjects 5-(m-methylphenoxy)-2-(1H)pyrimidinone is rapidly and efficiently metabolically converted to 5-m-tolyloxyuracil. The literature teaches that 5-substituted uracils such as 5-fluorouracil are metabolically converted to 5,6-dihydrouracils which undergo ring opening with subsequent loss of the $C_2$ pyrimidine carbon as carbon dioxide. We have discovered that 5-m-tolyloxyuracil unexpectedly does not undergo this metabolic degradation in rats and monkeys. Finally, we have discovered that 5-m-tolyloxyuracil has a much longer plasma half life in human subjects than does 5-(m-methylphenoxy)-2-(1H)pyrimidinone.

SUMMARY OF THE INVENTION

This invention comprises the compound of the formula:

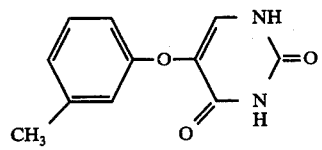

in substantially pure form and also in unit dosage form comprising from about 50–600 mg in a pharmaceutically acceptable diluent, and pharmaceutically acceptable salts thereof. Further, this invention comprises the method of treating peptic ulcer disease which comprises administering to an afflicted subject an effective amount of a compound of the formula above, 5-m-tolyloxyuracil also known as 5-m-methylphenoxyuracil.

The compound of this invention can exist in either the keto or enol forms and it is to be understood that we include both forms in the claims and disclosure in the present case, and that both forms fall within the scope of the present invention. Furthermore, we include in the present invention the pharmaceutically acceptable nontoxic metal salts such as the sodium, and potassium salts; and ammonium and substituted ammonium salts.

DETAILED DESCRIPTION OF THE INVENTION

For the preparation of 5-m-tolyloxyuracil the starting materials used are commercially available materials such as m-cresol and an ester of an alpha halo acetic acid such as bromo or chloro methyl or ethyl acetate. The m-cresol is condensed with a suitable base such as an alkali metal hydroxide or alkoxide, for example sodium or potassium hydroxide or sodium methoxide or ethoxide in a suitable solvent such as a lower alcohol, for example, methanol or ethanol. The resulting m-cresolate is reacted with an alpha halo acetic acid ester such as chloro or bromo, methyl or ethyl acetate to form a m-tolyloxy acetic acid ester such as methyl or ethyl m-tolyloxyacetate. The ester may be purified by distillation or may be used without further purification.

The methyl or ethyl m-tolyloxyacetate in a suitable solvent such as diethyl ether, benzene, toluene or tetrahydrofuran in the presence of a strong base such as potassium tertiary butoxide or sodium hydride is condensed with a formic acid ester such as methyl or ehtyl formate to give the alkali metal salt of an α-formyl-m-tolyloxy acetic acid ester such as sodium or potassium α-formyl-m-tolyloxy methyl or ethyl acetate. The salt can be isolated by filtration or can be used without further purification.

The alkali metal salt of an α-formyl-m-tolyloxy acetic acid ester in a suitable solvent such as a lower boiling alcohol is condensed with thiourea in the presence of variable quantities of a base such as an alkali metal hydroxide or alkoxide. The resulting product — the alkali metal salt of 5-(m-tolyloxy)-2-thiouracil is treated with a mineral acid such as hydrochloric or sulfuric acid to precipitate 5-(m-tolyloxy)-2-thiouracil. This material can be purified by precipitation from dilute sodium hydroxide with a mineral acid such as hydrochloric or acetic acid or by crystallization from a suitable solvent.

5-(m-Tolyloxy)2-thiouracil is treated with an equivalent or excess quantity of an alpha halo acetic acid such as chloro acetic acid and heated in an aqueous mineral acid. The resulting hydrolysis product 5-(m-tolyloxy)uracil is isolated by filtration and may be purified by slurrying with a solvent such as water, acetone or a lower alcohol such as methanol or ethanol.

The term peptic ulcer disease has historically been used to describe disease characterized by ulceration of the upper gastrointestinal tract and includes the disease characterized by ulceration of the body of the stomach, commonly called gastric ulcer disease as well as the disease characterized by ulceration of the duodenum, commonly called duodenal ulcer disease. Those skilled in the art and knowledgeable in the gastrointestinal literature now recognize that these two diseases are different from each other. Nevertheless, it is in its historical sense that we now use the term peptic ulcer disease.

Patients suffering from gastric ulcer disease, as a group do not suffer from excessive secretion of hydrochloric acid in the stomach. The cause of the disease is generally believed to be an imbalance between the "aggressive" forces in the stomach such as acid, pepsin and bile salts and the "defensive" forces in the stomach which consist of the gastric mucus layer and a gastric mucosal barrier which prevents the harmful diffusion of hydrochloric acid from the lumen of the stomach back through the gastric mucosa.

The drug Carbenoxolone-Na is known to protect animals from experimentally-induced gastric ulceration and in human gastric ulcer patients has been shown in numerous clinical trials to be an effective gastric antiulcer agent. 5-m-tolyloxyuracil, like Carbenoxolone-Na, protects rats against ulceration. Accordingly, 5-m-tolyloxyuracil may be expected to be clinically effective as a gastric antiulcer agent in man.

U.S. Pat. No. 3,922,345 discloses the method of treating peptic ulcers which comprises administering to a subject afflicted therewith a daily dose of about 0.60 to 21 mg per kg. of body weight of 5-(m-methylphenoxy)-2-(1H)-pyrimidinone. We have discovered that in rats, monkeys and human subjects 5-(m-methylphenoxy)-2-(1H)pyrimidinone is rapidly and efficiently metabolically converted to 5-m-tolyloxyuracil. Moreover, we have made the discovery that, contrary to previous teachings in the literature, other possible metabolic modifications of 5-(m-methylphenoxy)-2-(1H)pyrimidinone do not occur to any detectable extent. We have been unable to detect metabolic products resulting from (1) phenoxy ring hydroxylation, (2) oxidation of the m-methyl group or (3) ether cleavage.

Moreover, contrary to the teachings in the literature, we have discovered that 5-m-tolyloxyuracil possesses unusual metabolic stability. The literature teaches that a 5-substituted uracil such as 5- fluorouracil undergoes a reduction of the 5,6-double bond to give a 5,6-dihydrouracil which subsequently undergoes ring opening to an N-acetamido β-alanine which then loses the C-2 pyrimidine carbon as carbon dioxide.

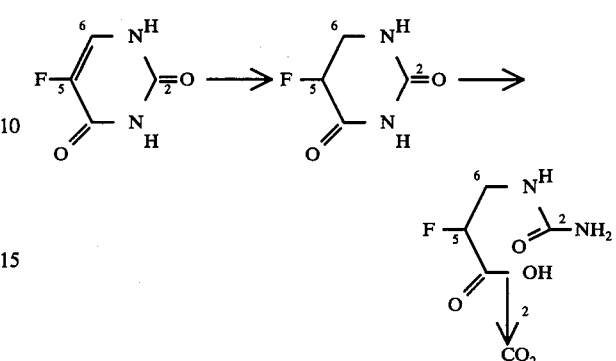

In studies in rats and the monkey using 5-m-methylphenoxy-2-(1H)-pyrimidinone containing a radioactively labelled carbon at $C_2$ of the pyrimidine ring we have shown that the metabolic instability observed with 5-fluorouracil does not occur with 5-m-tolyloxyuracil since no appriciable quantities of radioactive $CO_2$ were observed from the endogenously generated 5-m-tolyloxyuracil.

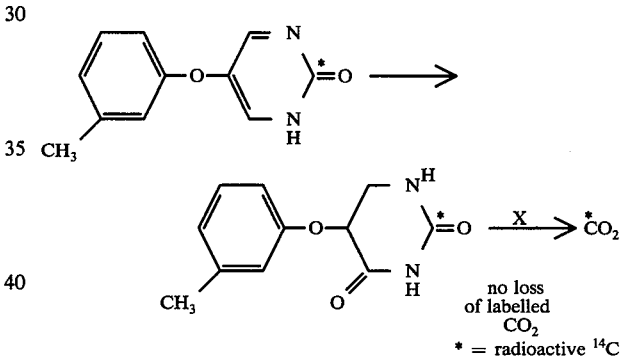

* = radioactive $^{14}C$

We have also discovered in studies in human subjects that 5-m-tolyloxyuracil has a much longer plasma half-life and reaches peak concentrations greater than does 5-(m-methylphenoxy)-2-(1H)-pyrimidinone. In man, using single doses of 400 to 700 mg of 5-(m-methylphenoxy)-2-(1H)pyrimidinone, this drug had declined below the level of detectability by 2 hours post dose. In marked contrast, endogenously generated 5-m-tolyloxyuracil reached peak concentrations greater than that of parent drug 4 hours post-dose and the half-life varied from 12.6 to 15.5 hours.

In our studies in animals and man we have never been able to isolate 5-m-tolyloxyuracil in substantially pure form. Rather we have obtained samples of urine and blood plasma from animals and man consisting of a multitude of natural components, one of which we have identified as 5-m-tolyloxyuracil by comparison of its physical properties with material prepared in substantially pure form by the synthesis described in the present application. Indeed, in samples of plasma from human subjects treated with 5-m-tolyloxy-2(1H)pyrimidinone we have only detected peak levels of 5-m-tolyloxyuracil at the very low concentration of 40 ug/ml. When we say "in substantially pure form", we mean a purity of 95% or greater.

In order to test the antiulcer activity of 5-m-tolyloxyuracil, stress induced gastric ulceration was produced by immobilizing non-fasted, female rats in a supine position and placing them in a refrigerator at 12° C. for 3 hours. Experimental drugs were administered 3 hours before the initiation of the cold-restraint stress period. At the conclusion of the stress period, the rats were sacrificed, their stomachs inflated with 5 ml of water and removed. The isolated stomachs were placed in a 4 percent aqueous solution of formaldehyde to stiffen the serosal side of the inflated stomach. This procedure facilitates examination of the stomach which is accomplished by slitting the stomach along its greater curvature and noting the number and incidence of gastric lesions. Both control and experimental drug groups consisted of ten rats. A significant reduction in the number and incidence of gastric lesions characterizes antiulcer agents.

The table below compares 5-m-tolyoxyuracil (Compound A) with 5-m-tolyloxy-2-thiouracil (Compound B), Carbenoxolone-Na (Compound C), and 5-(m-methylphenoxy)-2(1H)-pyrimidinone (Compound D).

| Compound | Dose | % incidence of lesions | Number of lesions | P Value |
|---|---|---|---|---|
| Compound A | 50 ip | 70 | 34 | < 0.05 |
| | control | 100 | 58 | |
| | 32 ip | 56 | 19 | < 0.05 |
| | control | 100 | 58 | |
| Compound B | 10 po | 80 | 50 | .51 |
| | control | 80 | 31 | |
| Compound C | 60 ip | 25 | 7 | < 0.05 |
| | control | 65 | 24 | |
| | 32 ip | 40 | 9 | > 0.05 |
| | control | 50 | 15 | > 0.05 |
| Compound D | 32 ip | 40 | 13 | < 0.05 |
| | control | 90 | 34 | |
| | 10 ip | 60 | 12 | < 0.05 |
| | control | 90 | 42 | |

Compounds A and D are effective antiulcer agents at both doses tested since the number and incidence of lesions following drug treatment are significantly lower (P value < 0.05) than in controls. Compound B is inactive. Compound C is significantly active (P < 0.05) the 60 mg/kg dose but is less active at 32 mg/kg at which dose the activity is not significant at the P = 0.05 level. Percent incidence of lesions is defined as follows.

$$\frac{\% \text{ Incidence}}{\text{lesions}} = \frac{\text{No. of animals with ulcers}}{\text{Total No. of animals in experimental group}} \times 100$$

Number of lesions is the total number of lesions in the experimental group.

The compound of the invention when used as an antiulcer agent can be administered alone, but will generally be administered in admixture with a pharmaceutical carrier selected with regard to the intended route of administration and standard pharmaceutical practice. For example, they may be administered orally in the form of tablets containing such excipients as starch and lactose, or in capsules either alone or in admixture with excipients, or in the form of elixirs or suspensions containing flavoring or coloring agents. They may be injected parenterally, for example, intramuscularly or subcutaneously. For parenteral administration, they are best used in the form of a sterile aqueous solution which may contain other solutes, for example, enough salts or glucose to make the solution isotonic.

With respect to dosage levels, a broad dosage range of 10 to 1000 mg/day for adults will be appropriate, a particularly preferred range being from 150 to 600 mg/day. The physician in any event will determine the actual dosage which will be most suitable for an individual patient and it will vary with age, weight and response of the particular patient. The above dosages are exemplary of the average host. There can, of course, be individual cases where higher or lower dosage ranges are merited, and such are within the scope of this invention.

The following example is illustrative and in no way limits the scope of the appended claims.

EXAMPLE I

Step A

To a solution of sodium ethoxide prepared from 25 g (1.1 mol) sodium metal in 800 ml ethanol was added 108 g (1.0 mol) m-cresol. After warming at reflux for 1.5 hr, 167 g (1.0 mol) ethyl bromoacetate was added dropwise as reflux continued. After 5.5 hr reflux, the reaction mixture was cooled and NaBr removed by filtration. The filtrate was concentrated to 200 ml volume and extracted with 3 × 300 ml ether. The combined ether layers were washed with pH 10.5 NaOH solution, saturated NaCl solution and were dried over anhydrous $MgSO_4$. The ether was removed under reduced pressure and the residual yellow oil distilled at 105°/1 mm Hg to give 115.3 g m-tolyloxyethyl acetate.

Step B

To a slurry of 30.3 g (0.63 mol) of a 50% NaH-mineral oil description in 300 ml diethyl ether was added dropwise a solution of 45 g (0.61 mol) ethyl formate and 115.3 g (0.60 mol) m-tolyloxyethyl acetate. Gentle warming of the ether solution during the addition initiated a reaction and a thick white precipitate formed. After stirring for 3 hours an additional 600 ml diethyl ether was added and the resulting white salt was isolated by filtration to give 90.9 g sodium salt of ethyl α-formyltolyloxy acetate.

Step C

To a slurry of 90.9 g (0.40 mol) of the sodium salt of ethyl α-formyltolyloxyacetate in 800 ml of a sodium ethoxide solution formed from 9.9 g (0.41 mol) sodium metal was added 61 g (0.80 mol) thiourea and the mixture was heated at reflux 1.5 hr. On cooling the amber solution was filtered from a small quantity of dark brown tarry solid and added dropwise to a well stirred solution of 100 ml glacial acetic acid in 800 ml $H_2O$ to precipitate a fine granular white solid. This was washed well with $H_2O$ and dried to give 59.9 g of 5-m-tolyloxy-2-thiouracil (m.p. 210°). An analytical sample was crystallized from acetone to give white needles m.p. 215°–216°.

Anal. Calc'd for $C_{11}H_{10}N_2O_2S$: C, 56.40; H, 4.30; N, 11.95. Found: C, 56.80; H, 4.13; N, 11.86.

Step D

To a solution of 73.3 g (0.744 mol) chloroacetic acid in 700 ml 12N HCl was added 28.6 g (0.122 mol) of 5-m-tolyloxy-2-thiouracil. The slurry was heated at reflux for 35 hours and filtered while still hot. The resulting white solid was washed well with $H_2O$ and dried to give 24.5 g of 5-m-tolyloxyuracil (m.p. 291°–295°).

Anal. Calc'd for $C_{11}H_{10}N_2O_3$: C, 60.55; H, 4.62; N, 12.83. Found: C, 60.57; H, 4.42; N, 12.55.

In marked contrast to the very low concentrations of 5-m-tolyloxyuracil admixed with a multitude of natural components in blood plasma and urine we have now prepared 5-m-tolyloxyuracil in quantities of as much as 24.5 g. in substantially pure form. In addition to a satisfactory carbon, hydrogen and nitrogen analysis we have also obtained additional spectroscopic data that supports the substantially pure form of the 5-m-tolyloxyuracil that we have prepared. We have examined the melting point behavior of 5-m-tolyloxyuracil using a Dupont 900 Differential Thermal Analyzer.

In our studies with 5-m-tolyloxyuracil we have obtained a differential thermal analysis curve which is consistent with a pure compound. This curve is illustrated in FIG. 1.

In addition to a satisfactory elemental analysis we have obtained further verification of the correct molecular formula of the 5-m-tolyloxyuracil we have prepared by the use of high resolution mass spectroscopy. Using a DS-50 mass spectrometry data system we have investigated the high resolution mass spectrum of the 5-m-tolyloxyuracil we have prepared in substantially pure form. The molecular formula of 5-m-tolyloxyuracil is $C_{11}H_{10}N_2O_3$. Based on a system calibrated on $C^{12}$ the exact mass of the $C_{11}H_{10}N_2O_3$ ion is 218.0691. In our experiment the measured mass of the parent ion we have observed is 218.0699. This value deviates from the expected value by only 0.8 parts per million. The formula of $C_{11}H_{10}N_2O_3$ is the only formula containing C, H, N, O whose exact mass lies within 5.0 parts per million of the experimentally observed value of 218.0699. This data therefore further supports the formula of $C_{11}H_{10}N_2O_3$ which we have assigned to 5-m-tolyloxyuracil.

What is claimed is:

1. A unit dosage form suitable for use in treating peptic ulcer disease comprising from about 50–600mg. of 5-m-tolyloxyuracil in a pharmaceutically acceptable diluent.

2. The method of treating peptic ulcer disease which comprises orally or parenterally administering to a subject afflicted therewith an anti-ulcer effective amount of 5-m-tolyloxyuracil.

* * * * *